United States Patent [19]

Papenfuhs

[11] 4,234,513
[45] Nov. 18, 1980

[54] PROCESS FOR THE PREPARATION OF MONOARYL THIOUREAS

[75] Inventor: Theodor Papenfuhs, Frankfurt am Main, Fed. Rep. of Germany

[73] Assignee: Hoechst Aktiengesellschaft, Fed. Rep. of Germany

[21] Appl. No.: 36,687

[22] Filed: May 7, 1979

[30] Foreign Application Priority Data

May 10, 1978 [DE] Fed. Rep. of Germany ....... 2820321

[51] Int. Cl.$^3$ .................... C07C 157/09; C07C 69/14; C07C 69/78
[52] U.S. Cl. ......................................... 564/26; 560/9; 560/18; 560/106; 560/231; 564/27; 564/28
[58] Field of Search ...................... 260/552 A, 552 R; 560/9, 18, 106, 231

[56] References Cited

U.S. PATENT DOCUMENTS

| | | | |
|---|---|---|---|
| 3,395,233 | 7/1968 | Duerr et al. | 260/552 R X |
| 3,539,626 | 11/1970 | Gagneux | 260/552 A X |

FOREIGN PATENT DOCUMENTS

| | | | |
|---|---|---|---|
| 522682 | 3/1956 | Canada | 260/552 R |
| 645701 | 11/1950 | United Kingdom | 260/552 A |

*Primary Examiner*—John Doll
*Attorney, Agent, or Firm*—Connolly and Hutz

[57] ABSTRACT

An improved process for the preparation of monoaryl thiourea compounds, in which a salt of an arylamine is reacted with ammonium rhodanide or an alkali metal rhodanide in an aqueous medium; the improvement consists in that the reaction is carried out in a reaction mixture which at the start contains a higher amount by weight of the salt of the arylamine than of water and contains 1 to 1.25 times the equivalent amount of the rhodanide calculated on the arylamine, and which does not contain any excess acid, and that the reaction is carried out at a temperature which is below the boiling point of the reaction mixture by at least 5° C. It is advantageous, but not compulsory, to effect the reaction while using from 5 to 10 mol % of hydrogeno-sulfite ions, in order to remove sulfur-containing by-products which are formed as a consequence of the acid spontaneous decomposition of the rhodanide in an inevitable side reaction.

By means of the improved novel process, homogeneous monoaryl thioureas are obtained in a high yield with a reduced charge of the waste water.

6 Claims, No Drawings

PROCESS FOR THE PREPARATION OF MONOARYL THIOUREAS

This invention concerns the improvement of a process for preparing monoaryl thioureas whose use in technology has been known from Houben-Weyl, Methoden der organischen Chemie, 4th Edition, Vol. 9, page 884 (1955), and Chem.Rev. 55, 181 (1955); they may also serve as precursors for the preparation of azo dyestuffs.

Of the approaches known from literature to the preparation of aryl thioureas (cf. Houben-Weyl, loc.cit., pages 885 et seq.), the reaction of arylamines with rhodanides is used in technology. Said reaction may in principle be carried out in an aqueous medium, the arylamines being employed advantageously in the form of mineral acid salts. However, besides the intended monoaryl thioureas there are formed N,N'-diaryl thioureas to a varying degree, whose amount according to Houben-Weyl (loc.cit. p. 887) increases with a rising concentration of the arylamine salts (cf. also A. Bertram, Ber.Dtsch.Chem.Ges. 25, 48 (1892)). The reaction in organic solvents (for example, chloroaromatic hydrocarbons, chloroaliphatic compounds, alcohols) proceeds in a more uniform manner (cf. Org.Synth., Coll. Vol. III, p. 77; J.Journ.Med. Chem. 15 (1972), 1024; Japanese Patent Publication Sho-49-1255); it is therefore preferred in technology.

Nevertheless, there have been numerous attempts to improve the synthesis of aryl thioureas in the aqueous medium with regard to the yield and the formation of homogeneous products in a way that it can compete also from an economical point of view with the reactions in solvents which are effected with very good yields. In order to suppress the formation of diaryl thiourea, it has been attempted without exception to operate in a higher dilution (cf. Chem.Ind. (London) 1974, pages 18 and 750; Belgian Patent Specification No. 603 595; Belgian Pat. Specification No. 765 477; Helv.Chim. .Acta 25, 515 (1942); Org. Synth., Coll. Vol. IV, p. 180). To obtain satisfactory yields, a large excess amount of rhodanide as the second starting compound and of mineral acid was frequently required. The work-up methods of these known processes involve in most cases a very high expenditure, for example due to repeated operations of evaporation to dryness, the reaction periods are very long, the space/time yields are too low, so that the processes are on the whole technically unsatisfactory. The yields of aryl thiourea which may be obtained according to these known processes are less than 75% of the theory, as a rule only between 30 and 60% of the theory. The processes are thus no longer interesting from the economical point of view, all the more since they additionally involve a high charge of the waste water, especially in cases where an excess amount of rhodanide and acid is used.

The known processes of operating in a high dilution (the starting concentration of the arylamine salts employed as starting compounds is in the range of from 4% by weight to 35% by weight at a maximum) were intended to largely suppress the formation of the diaryl thioureas. In spite of this measure and in addition to the above-mentioned drawbacks it is in most cases inevitable to effect a purification of the crude products obtained.

Due to these serious drawbacks, none of the processes known from literature and comprising the reaction of arylamines with rhodanides in an aqueous medium has gained any importance in technology so far.

There has now been found a process leading to a homogeneous monoaryl thiourea, in which a salt of an aromatic amine is reacted with ammonium rhodanide or an alkali metal rhodanide in an aqueous medium. The process improvement is effected by starting from an aqueous reaction mixture in which the salt of the aromatic amine is contained in a higher amount by weight than the water serving as reaction medium, and in which the ammonium or alkali metal rhodanide is used in at least the amount stoichiometrically necessary and at most with a molar excess of 25%, and which does not have any excess acid, and by performing the reaction at a temperature which is below the boiling point of the reaction mixture by at least 5° C., preferably at least 10° C., the boiling point of the reaction mixture depending essentially on the pressure applied (normal pressure or elevated pressure in a closed vessel or autoclave).

The present invention therefore provides a process for the preparation of a monoaryl thiourea compound by reacting a salt of an aromatic amine (arylamine) with ammonium rhodanide or an alkali metal rhodanide, such as sodium or potassium rhodanide, in an aqueous medium, which comprises carrying out the reaction in a reaction mixture which at the start contains a higher amount by weight of the salt of the arylamine than of water and from 1 to 1.25 times, preferably from 1.05 to 1.10 times the equivalent amount of the ammonium rhodanide or alkali metal rhodanide, calculated on the arylamine used, and which does not contain any excess acid, and carrying out the reaction at a temperature which is below the boiling point of the reaction mixture by at least 5° C., preferably by at least 10° C.

The presence of free acid which due to the rhodanide decomposition may to a certain degree adversely affect the reaction, as will be shown later, cannot be avoided, since due to the low basicity of the arylamines at least the salts of the mineral acids with the arylamines are present in a chemical equilibrium with the dissociated acid, free acid thus being present in the reaction mixture. For this reason, the arylamine salt is only allowed to be formed in a stoichiometrical amount with the acid thereof, and an excess of acid has to be excluded.

The reaction of the highly concentrated reaction mixture optionally being present as suspension is advantageously carried out while stirring the said mixture or constantly mixing it by other means common in technology. In order to reach a sufficiently high reaction velocity, the reaction is carried out preferably at a temperature of at least 50° C. In accordance with the known physical laws the boiling point of the reaction mixture depends on the concentration of the aqueous reaction medium and the pressure applied. For the highly concentrated solutions and/or suspensions present in this case, a boiling point of from 107° to 110° C. has to be expected at normal pressure (atmospheric pressure); when applying an overpressure of, for example, 3 bars, e.g. in a closed vessel, the boiling point of the reaction mixture is in the range of from about 130° to 135° C. The exact boiling point may be easily determined for the respective case by way of a preliminary test.

According to the process of the invention monoaryl thiourea compounds having a melting point of more than 100° C. can easily be prepared in a high yield as well as with a high technical purity, said compounds being unsubstituted in the aryl radical or substituted by slightly electronegative, electroneutral and/or electropositive substituents. Nitro groups, sulfo groups and cyano groups, for example, are excluded as being strongly electronegative substituents. The aryl radical in the arylamine as starting compound and/or in the monoaryl thiourea as final product represents an aromatic carbocyclic radical, especially the radical of a benzene nucleus or a naphthalene nucleus, which may be substituted by slightly electronegative, electroneutral and/or electropositive substituents.

Substituents of this kind are, for example, lower alkyl groups, such as methyl, ethyl or propyl groups, the hydroxy group, lower alkoxy groups, such as methoxy, ethoxy, propoxy or butoxy groups, lower alkoxyalkyl groups, aryloxy groups, such as the phenoxy group being unsubstituted or substituted by lower alkyl, lower alkoxy and/or chlorine, amino groups optionally being substituted by lower aliphatic radicals and/or aryl radicals, such as phenyl radicals, acylamino groups or lower alkyl ester groups, such as those derived from lower aliphatic carboxylic acids or from arylcarboxylic acids, such as from benzoic acid, lower alkylmercapto or arylthio radicals, such as the phenylthio radical, or acyloxy groups of lower aliphatic carboxylic or arylcarboxylic acids, such as of benzoic acid. Slightly negative groups are especially halogen atoms, such as fluorine, chlorine or bromine atoms, lower alkanoyl or lower alkoxycarbonyl groups, aryloyl radicals, such as the benzoyl radical, or the carbonamide and sulfonamide groups unsubstituted or mono- or disubstituted by lower alkyl and/or phenyl.

The term "lower" to be found in the following relates to alkyl or alkylene groups of from 1 to 4 carbon atoms, of which the above-mentioned compounds or radicals are partially or completely composed.

Arylamines containing two primary amino groups may be employed selectively—depending on the use of one or two mols of the rhodanide and the acid required for the salt formation—for the preparation of a monoaryl thiourea compound and/or an arylene-bis-thiourea compound.

The process of the invention proceeds in a uniform manner and gives high yields of technically pure monoaryl thioureas. It is particularly appropriate for the preparation of monophenyl thiourea and mononaphthyl thiourea compounds and the derivatives thereof which are substituted in the benzene or naphthalene nucleus by electropositive, electroneutral and/or slightly electronegative groups. For preparing these compounds there are correspondingly used as starting products the unsubstituted phenylamines and/or naphthylamines or said compounds being substituted by the above-mentioned groups.

According to the process of the invention preference is given to the preparation of a monophenyl-thiourea compound of the formula (1)

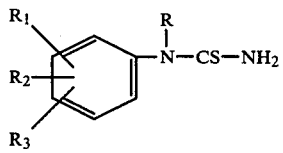

in which R is hydrogen or lower alkyl, such as methyl or ethyl, $R_1$ is hydrogen or fluorine, chlorine, bromine, lower alkyl, such as methyl or ethyl, lower alkoxy, such as methoxy or ethoxy, hydroxy, amino, phenylamino, phenoxy, lower monoalkylamino, lower dialkylamino or carbamoyl, $R_2$ is hydrogen, chlorine, lower alkyl or lower alkoxy, and $R_3$ is hydrogen, lower alkyl or lower alkoxy, the formula radicals R, $R_1$, $R_2$ and $R_3$ may have the same meanings or are different from one another. For the preparation of the compounds of the formula (1) there are correspondingly used as a starting compound an aniline compound of the formula (2)

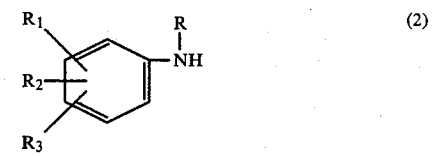

in which R, $R_1$, $R_2$ and $R_3$ are defined above.

Arylamines which may be employed with particular advantage as starting compounds for the process of the invention are, for example, aniline, the various toluidines and xylidines, medisine, the various anisidines and phenetidines and the corresponding thioether compounds thereof, the various halogeno-anilines (with fluorine, bromine and especially chlorine being understood by halogen), the various halogeno-toluidines and halogen-anisidines, these halogeno compounds optionally containing 1, 2 or 3 halogen substituents, furthermore the various aminophenols and phenylene diamines; the said arylamino compounds may contain the amino group in the form of the primary amine or in the form of a secondary alkylamine. If the arylamine merely is a primary amino compound (R=H), arylamines to be used in accordance with the invention are, for example, the various amino-acetophenones and amino-benzophenones, furthermore the amino-benzoic-alkyl acid esters, the aminodiphenyl ethers and -thioethers, the aminonaphthalenes and the compounds thereof being substituted in the aromatic nucleus by lower alkyl, lower alkoxy and/or halogen.

It is furthermore advantageous, but not compulsory, to effect the reaction while using 5 to 10 mol % of hydrogenosulfite ions. The presence of hydrogenosulfite ions ensures a clean outgoing air without bad smell, also when carrying out the process of an industrial scale. The addition of hydrogenosulfite is recommended because during the reaction of the invention an acid spontaneous decomposition of the rhodanide occurs as an inevitable side reaction which yields sulfur-containing products with the oxidation step of the hydrogen sulfide; these sulfides being formed are bound by the hydrogenosulfite while forming thiosulfate. Due to this side reaction and in order to obtain high yields, it is recommended to use not only the required stoichiometrical amount of rhodanide as second starting component, but a small excess amount for the reaction mixture; however, for reasons of pollution control of the waste water, an excess of rhodanide of more than 25 mol % should be avoided although it does not influence the quality of the reaction products, i.e. the monoaryl thiourea compounds, or the reaction procedure. In view of the acid spontaneous decomposition of the rhodanide the presence of free acid in the reaction mixture is therefore to be avoided.

As salts of arylamines there may be mentioned the arylamine salts of strong acids, especially the salts of strong mineral acids, such as hydrobromic acid, sulfur acid, phosphoric acid and especially hydrochloric acid.

The formation of the salt from the arylamine and acid must therefore be effected in stoichiometrically equivalent amounts. An excess amount of acid results in the above-mentioned decomposition reactions of the rhodanide and thus in reduced yields; especially in consequence of the low-valency sulfur compounds which are formed and set free as ill-smelling and toxic waste gases, such a process would be technically inadmissible. But also in cases where part of the arylamine is present as a free base due to an acid deficiency in the preparation or formation of the arylamine salt, there results a considerable yield reduction since this mode of proceeding leads to the formation of far less pure arylthiourea compounds which require subsequent purification operations.

The reaction mixture may be formed, for example, by dissolving or suspending the arylamine salt, preferably the salt of a mineral acid of the arylamine, in an amount by weight of water which is smaller than that of the salt, or by dissolving or suspending the arylamine in a stoichiometrical amount of an aqueous solution of the strong acid, such as mineral acid, the water content of the acid solution being calculated in a way that its amounts by weight remains less than that of the arylamine salt formed. Subsequently there are added to this arylamine salt solution or suspension the rhodanide and optionally an alkali metal hydrogenosulfite, such as sodium hydrogenosulfite, in a solid form or in a concentrated aqueous solution, taking care, when using aqueous solutions, that the total amount of water in the reaction mixture thus prepared remains less by weight than that of the arylamine salt.

As for the execution of the reaction itself, it may be conducted, for example, as follows: The reaction mixture is heated, preferably to a temperature of more than 45° C.; the reaction may be carried out advantageously in the temperature range of from about 50° to 100° C. as well as in the range of from 5° to 10° C. below the boiling temperature of the reaction mixture. The temperature range should be chosen in a way that final products as pure as possible are obtained and in a good yield, without quality-reducing impurities being present in the final product; this temperature range can easily be determined by way of a preliminary test for each desired final product. Impurities in the final product will be formed when during the reaction of the arylamine salt with the rhodanide an oily or greasy phase is passed, in the course of which starting compounds may be included in that oily or greasy phase; thereby the reaction of the components itself is impeded, the yield thus reduced and the desired monoarylurea rendered impure. The risk of impurities is not present if the final product separates in a crystalline form. The temperature range should therefore be chosen in a way that those oily or greasy phases during the reaction process do not occur; said range may easily be determined for every starting mixture and/or for every reaction for preparing a determined intended final product (aryl thiourea) by means of a rapid preliminary test which is easy to perform by a person skilled in the art. Preferred and advantageous temperature ranges of the reaction according to the invention for different starting amines for preparing the corresponding monoaryl thiourea final products have been indicated in the following Examples.

In order to reduce the reaction time, the reaction temperature may be increased after the final product has started to separate in a crystalline form, but merely to a temperature which is at most 5° C., preferably at most 10° C. below the boiling point of the reaction mixture; when higher temperatures than those obtainable and allowed under atmospheric pressure are to be applied, the reaction may be carried out under pressure, however, generally the reaction can be carried out with good success at atmospheric pressure. High reaction temperatures of 5° C. below the boiling point of the reaction mixture with the possible application of pressure will only be preferred occasionally and in special cases in order to obtain a higher space/time yield.

The limitation of the reaction temperature, especially of the final temperature of the reaction, to at most 5° to 10° C. below the boiling point is a decisive factor for the quality of the final product. The reason is that the reaction of the arylamine salt with the rhodanide to give the intended monoaryl thiourea compound is in the undesirable reaction equilibrium while forming the corresponding diaryl thiourea compound. This side reaction is restrained and suppressed under the applied conditions of the invention and process parameters, especially by the application of a high concentration of the arylamine salt in the reaction mixture and the limitation of the maximum temperature. On the contrary, if the process is carried out at boiling temperature itself, the diaryl thiourea compounds which are largely volatile with steam are removed by distillation from the reaction mixture by separating in the condenser or in the distillate, due to which fact the reaction equilibrium between the starting components, monoaryl thiourea and diaryl thiourea must constantly be re-adjusted and the diaryl thiourea compound is formed in a reversible manner from the monoaryl thiourea compound already produced. In this manner the yield and the quality of the intended monoaryl thiourea are considerably reduced.

Especially owing to the high concentration of the arylamine salt used according to the invention in the reaction mixture the novel process leads to a considerable increase of the yield and also of the purity of the product as compared with the state of the art; thus, the process of the invention permits a practically quantitative reaction of the starting components to give the intended monoaryl thiourea final product within a relatively short and thus economically favorable reaction period. The yields are generally above 90% of the theory, and as a rule the yields are in the range of from 95 to 98% of the theory. The space/time yield in the process of the invention is very high, whereas the charge of the waste water has been markedly reduced as compared with the known processes.

The following Examples serve to illustrate the invention. The parts are parts by weight and the percentages are percent by weight, unless otherwise stated.

EXAMPLE 1

738 Parts of p-anisidine, 502 parts of ammonium rhodanide and 78 parts of a 40% aqueous sodium bisulfate solution are introduced successively, while stirring, into 1050 parts of 20% aqueous hydrochloric acid. This mixture is heated to 95° to 100° C. and stirred for 12 to 15 hours at this temperature. Thereafter the precipitate having been formed is filtered off with suction, while hot, washed with hot water until neutral and dried. 1038 Parts (corresponding to 95.1% of the theory) of 4-methoxyphenyl thiourea of the formula

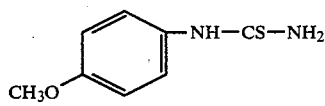

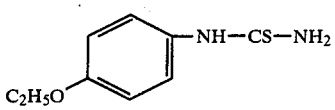

are obtained, the compound having a melting point of from 200° to 201° C.

If the ammonium rhodanide is replaced by an equivalent amount of sodium or potassium rhodanide, the 4-methoxyphenyl thiourea is obtained in an equally high yield and quality.

EXAMPLE 2

558 Parts of aniline, 479 parts of ammonium rhodanide and 78 parts of a 40% aqueous sodium bisulfite solution are introduced successively into 592 parts of a 37% aqueous hydrochloric acid. This reaction mixture is at first stirred for 8 hours at 80° C., then for 8 hours at 90° C., thereafter cooled to 20° C.; the precipitate formed is filtered off with suction, washed until neutral and dried. 888 Parts (corresponding to 97.4% of the theory) of phenyl thiourea are obtained, which product has a melting point in the range of from 148° to 150° C.

If instead of the 37% hydrochloric acid there is used an equivalent amount (=980 parts) of a 30% aqueous sulfuric acid, the phenyl thiourea is obtained in an equally high yield and quality.

EXAMPLE 3

750 Parts of a 30% aqueous hydrochloric acid are placed into a reaction vessel, whereupon 822 parts of p-phenetidine, 479 parts of ammonium rhodanide and 31.2 parts of sodium hydrogenosulfite are introduced successively, while stirring. The reaction mixture is stirred for 15 hours at 80° C., thereafter for 8 hours at 95° C., and subsequently the precipitate having been formed is filtered off with suction, while hot, and washed with hot water until neutral. The dried product gives a yield of 1129 parts (corresponding to 96.0% of the theory) of p-ethoxyphenyl thiourea of the formula which product has a melting point of from 167° to 168° C.

If the sodium bisulfite is replaced by an equivalent amount of potassium or ammonium bisulfite, the p-ethoxyphenyl thiourea may be prepared in an equally high yield and quality.

EXAMPLE 4

A mixture of 592 parts of 37% hydrochloric acid, 642 parts of o-toluidine, 570 parts of ammonium rhodanide and 78 parts of a 40% aqueous sodium bisulfite solution is stirred for 4 hours at 60° C., thereafter for 4 hours at 70° C. and finally for 8 hours at 80° C.; it is then cooled to 20° C., and the precipitate having been formed is filtered off with suction, washed until neutral and dried.

950 Parts (corresponding to 95.4% of the theory) of 2-methylphenyl thiourea are obtained, the compound having a melting point of 156° C.

If the reaction is carried out without sodium bisulfite, the 2-methylphenyl thiourea is obtained in the same yield with little reduced quality, the compound then shows a melting point of 154° C.

EXAMPLES 5 to 38

According to the process of invention, as for example analogously to a variant as described in one of the preceding Examples, the aryl thioureas corresponding to the formula (1) which are indicated by their starting amino compounds in the following Table Examples can be prepared with the yields and qualities stated therein (characterized by the melting point of the final product obtained). The reaction conditions which may be used are shown therein. The corresponding starting compound figures as arylamine hydrochloride (prepared from stoichiometrical amounts of the arylamine of the formula (2) and aqueous hydrochloric acid with the content of HCl indicated therein), said arylamine hydrochlorides being employed for the reaction mixture in the form of this hydrochloric solution or suspension.

| Example | Arylamine of the formula (2) (1 mol) | NH$_4$SCN (mol) | Strength of HCl in % b.w. | Reaction temp. (°C.) | period (h) | yield (% of th.) | M.p. (°C.) |
|---|---|---|---|---|---|---|---|
| 5 | m-toluidine | 1.05 | 37.0 | 70 | 20 | 86.6 | 110 |
| 6 | p-toluidine | 1.05 | 20.0 | 80/100 | 2/5 | 91.0 | 188 |
| 7 | o-anisidine | 1.05 | 20.0 | 80/90 | 8/8 | 95.6 | 152 |
| 8 | m-anisidine | 1.05 | 20.0 | 80/90 | 8/8 | 90.1 | 160 |
| 9 | m-aminophenol | 1.05 | 20.0 | 80/90 | 8/8 | 79.0 | >230 |
| 10 | p-aminophenol | 1.05 | 20.0 | 80/90 | 8/8 | 89.0 | 215 |
| 11 | o-chloroaniline | 1.05 | 20.0 | 80/100 | 8/8 | 98.2 | 146 |
| 12 | m-chloroaniline | 1.05 | 20.0 | 80/90 | 8/12 | 93.3 | 135 |
| 13 | p-chloroaniline | 1.05 | 20.0 | 80/90 | 8/8 | 94.5 | 178 |
| 14 | p-phenylene diamine | 1.05 | 30.0 | 80/90 | 8/8 | 91.2 | 190 |
| 15 | p-phenylene diamine | 2.10 | 20.0 | 80/100 | 8/8 | 93.2 | 230 |
| 16 | p-dimethylamino-aniline | 1.05 | 20.0 | 80/90 | 8/10 | 91.9 | 180 |
| 17 | 2-(β-methoxy-ethoxy)-aniline | 1.25 | 37.0 | 70 | 20 | 82.8 | 145 |
| 18 | p-acetylamino-aniline | 1.05 | 20.0 | 80/90 | 8/8 | 88.9 | 201 |
| 19 | p-aminobenzamide | 1.05 | 20.0 | 80/100 | 4/12 | 87.2 | 229 |
| 20 | p-aminobenzoic acid ethyl ester | 1.05 | 20.0 | 80 | 7 | 98.2 | 157 |
| 21 | p-amino-benzophenone | 1.05 | 20.0 | 80/90 | 8/8 | 89.7 | 179 |
| 22 | 2,4-dimethyl-aniline | 1.05 | 20.0 | 80/90 | 8/8 | 87.2 | 174 |

-continued

| Example | Arylamine of the formula (2) (1 mol) | NH₄SCN (mol) | Strength of HCl in % b.w. | Reaction temp. (°C.) | period (h) | yield (% of th.) | M.p. (°C.) |
|---|---|---|---|---|---|---|---|
| 23 | 2,5-dimethyl-aniline | 1.05 | 37.0 | 70 | 20 | 95.6 | 136 |
| 24 | 2,4-dimethoxy-aniline | 1.05 | 20.0 | 70/80 | 5/15 | 81.1 | 194 |
| 25 | 2,5-dimethoxy-aniline | 1.05 | 20.0 | 70/80 | 5/15 | 91.1 | 163 |
| 26 | 2,5-diethoxy-aniline | 1.05 | 20.0 | 70 | 16 | 84.2 | 151 |
| 27 | 2-methyl-5-chloro-aniline | 1.05 | 30.0 | 80 | 12 | 89.7 | 165 |
| 28 | 2-methyl-4-chloro-aniline | 1.10 | 20.0 | 80/90 | 4/12 | 93.8 | 153 |
| 29 | 4-methyl-2-chloro-aniline | 1.05 | 20.0 | 80/90 | 8/8 | 85.9 | 167 |
| 30 | 2-methoxy-4-chloro-aniline | 1.05 | 20.0 | 70 | 16 | 83.9 | 159 |
| 31 | 2,3-dichloroaniline | 1.05 | 20.0 | 80 | 9 | 86.2 | 140 |
| 32 | 2,4-dichloroaniline | 1.10 | 25.0 | 80/100 | 4/8 | 94.0 | 146 |
| 33 | 2,5-dichloroaniline | 1.05 | 20.0 | 80/90 | 8/4 | 90.5 | 184 |
| 34 | 5-amino-benzimidazolone | 1.05 | 10.0 | 80/90/100 | 4/4/5 | 95.9 | >320 |
| 35 | 2-methoxy-5-methyl-4-chloroaniline | 1.05 | 20.0 | 80 | 8 | 96.4 | 170 |
| 36 | 2,4-dimethoxy-5-chloroaniline | 1.05 | 20.0 | 80/90 | 5/8 | 89.3 | 186 |
| 37 | 2,5-dimethoxy-4-chloroaniline | 1.05 | 20.0 | 80/90 | 6/6 | 91.6 | 79 |
| 38 | N-ethyl-aniline | 1.05 | 37.0 | 80 | 20 | 80.5 | 113 |

What is claimed is:

1. In a process for the preparation of a monoaryl thiourea compound by reacting a salt of an arylamine with ammonium rhodanide or an alkali metal rhodanide in an aqueous medium, the improvement which comprises carrying out the reaction in a reaction mixture which at the start contains a higher amount by weight of the salt of the arylamine than of water and from 1 to 1.25 times the equivalent amount of the ammonium rhodanide or alkali metal rhodanide calculated on the arylamine, and does not contain any excess acid, and carrying out the reaction at a temperature which is below the boiling point of the reaction mixture by at least 5° C.

2. A process according to claim 1, which comprises carrying out the reaction while using from 5 to 10 mol % of hydrogenosulfite ions.

3. A process according to claim 1 or 2, wherein the starting arylamine is an aniline or a naphthylamine which is unsubstituted or substituted by slightly electronegative, electroneutral and/or electropositive substituents.

4. A process according to claim 1 or 2, wherein the starting arylamine is an aniline or a naphthylamine which is unsubstituted or substituted by substituents selected from the group of lower alkyl, hydroxy, lower alkoxy, lower alkoxyalkyl, phenoxy, phenoxy substituted by lower alkyl, lower alkoxy and/or chlorine, amino, amino substituted by lower alkyl and/or phenyl, alkanoylamino, benzoylamino, alkylene-carbonyloxyalkyl with lower alkyl and alkylene, lower alkylmercapto, phenylthio, lower alkanoxyloxy, benzoyloxy, halogen, lower alkanoyl, lower alkoxycarbonyl, benzoyl, carbamoyl, sulfamoyl, carbamoyl mono- or disubstituted by lower alkyl and/or phenyl and sulfamoyl mono- or disubstituted by lower alkyl and/or phenyl.

5. A process according to claim 1 or 2, which comprises converting an arylamine of the general formula (2)

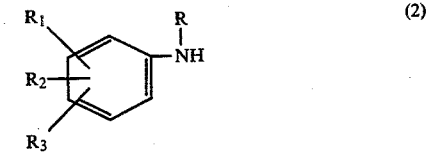

in which R is hydrogen or lower alkyl, R₁ is hydrogen, fluorine, chlorine, bromine, lower alkyl, lower alkoxy, hydroxy, amino, phenylamino, phenoxy, lower monoalkylamino, lower dialkylamino or carbamoyl, R₂ is hydrogen, chlorine, lower alkyl or lower alkoxy, and R₃ is hydrogen, lower alkyl or lower alkoxy, the formula radicals R, R₁, R₂ and R₃ being identical or different from one another, into a monphenyl thiourea of the general formula (1)

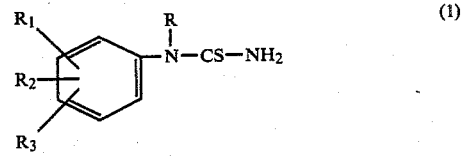

in which R, R₁, R₂ and R₃ are defined as above.

6. A process according to claim 1 or 2, which comprises carrying out the reaction at a temperature of at least 50° C.

* * * * *